(12) United States Patent
Osadchy et al.

(10) Patent No.: US 12,076,131 B2
(45) Date of Patent: Sep. 3, 2024

(54) CATHETER SHAPE AND POSITION DETECTION USING FLEXIBLE MAGNETIC SENSOR

(71) Applicant: Biosense Webster (Israel) Ltd., Yokneam (IL)

(72) Inventors: Daniel Osadchy, Haifa (IL); Meir Bar-Tal, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 456 days.

(21) Appl. No.: 16/866,883

(22) Filed: May 5, 2020

(65) Prior Publication Data

US 2021/0345902 A1 Nov. 11, 2021

(51) Int. Cl.
*A61B 5/00* (2006.01)
*A61B 5/06* (2006.01)
*A61B 5/287* (2021.01)
*G16H 50/20* (2018.01)

(52) U.S. Cl.
CPC .............. *A61B 5/062* (2013.01); *A61B 5/066* (2013.01); *A61B 5/287* (2021.01); *A61B 5/7235* (2013.01); *A61B 5/742* (2013.01); *G16H 50/20* (2018.01)

(58) Field of Classification Search
CPC ......... A61B 5/062; A61B 5/066; A61B 5/287; A61B 5/7235; A61B 5/742; A61B 2017/00026; A61B 2017/00053; A61B 2017/00243; A61B 2017/00292; A61B 2034/2051; A61B 2034/2072; A61B 5/063; A61B 34/20; A61B 5/06; G16H 50/20; G01R 33/02; G01R 33/06; G01R 33/0035; G01R 33/0206

See application file for complete search history.

(56) References Cited

U.S. PATENT DOCUMENTS

| | | | |
|---|---|---|---|
| 5,983,126 A | 11/1999 | Wittkampf | |
| 8,478,379 B2 | 7/2013 | Osadchy et al. | |
| 8,818,486 B2* | 8/2014 | Montag | A61B 5/062 324/207.13 |
| 10,441,187 B2* | 10/2019 | Afonso | A61B 5/6852 |

(Continued)

OTHER PUBLICATIONS

Fitzpatrick, R., "Vector Potential for the Magnetic Field." The University of Texas at Austin Lecture Series (Year: 2007).*

(Continued)

*Primary Examiner* — Serkan Akar
*Assistant Examiner* — Amal Aly Farag
(74) *Attorney, Agent, or Firm* — Volpe Koenig (57) ABSTRACT

Methods, apparatus, and systems for medical procedures are disclosed herein for receiving an input of a plurality of measured coordinates of a respective plurality of position transducers of a probe inside a body of a subject, receiving a measured voltage measurement output by the probe, determining a cost function based on a model of known mechanical properties of the probe compared to the measured coordinates with respect to shapes that can be assumed by the probe in the body and further based on an expected voltage value compared to the measured voltage measurement, selecting a shape based on the cost function, generating corrected coordinates of the points along the probe based on the shape and displaying a representation of the probe using the corrected coordinates.

20 Claims, 7 Drawing Sheets

(56) References Cited

U.S. PATENT DOCUMENTS

| | | |
|---|---|---|
| 2006/0173251 A1 | 8/2006 | Govari et al. |
| 2007/0038078 A1 | 2/2007 | Osadchy |
| 2008/0009711 A1 | 1/2008 | Govari et al. |
| 2010/0121174 A1* | 5/2010 | Osadchy ................ A61B 5/063 703/2 |
| 2012/0150022 A1* | 6/2012 | Bar-Tal ................ A61B 5/063 600/424 |
| 2020/0289025 A1* | 9/2020 | Dichterman ........... A61B 5/063 |

OTHER PUBLICATIONS

Extended European Search Report dated Sep. 23, 2021 for European Patent Application No. 21171962.0.

* cited by examiner

CATHETER SHAPE AND POSITION DETECTION USING FLEXIBLE MAGNETIC SENSOR

FIELD OF INVENTION

The present disclosure relates generally to sensing the position of an object placed within a living body, and specifically to detection and compensation for artifacts experienced during position sensing of a probe in a living body.

BACKGROUND

A wide range of medical procedures involve placing objects, such as sensors, tubes, catheters, dispensing devices, and implants, within the body. Position sensing systems have been developed for tracking such objects. For example, U.S. Pat. No. 5,983,126, to Wittkampf, whose disclosure is incorporated herein by reference, describes a system in which catheter position is detected using electrical impedance methods. U.S. Patent Application Publications 2006/0173251, to Govari et al., and 2007/0038078, to Osadchy, describe methods for sensing the position of a probe by passing electrical currents through the body between an electrode on the probe and a plurality of locations on a surface of the body. These methods likewise use the electrical impedance of the body in sensing probe position.

When using impedance-based measurement technology for determining the position of a probe (e.g., a catheter), it has been found that if the probe image is not constrained to assume realistic shapes and positions, sudden fluctuations can occur, which are disconcerting to the physician who is viewing the patient monitor. U.S. Patent Application Publication 2008/0009711, whose disclosure is incorporated herein by reference, describes methods for enhanced visualization of a probe when such measurement technologies are used by stabilizing a displayed image of the probe.

SUMMARY

Methods, apparatus, and systems for medical procedures are disclosed herein for receiving an input of a plurality of measured coordinates of a respective plurality of position transducers of a probe inside a body of a subject, receiving a measured voltage measurement output by the probe, determining a cost function based on a model of known mechanical properties of the probe compared to the measured coordinates with respect to shapes that can be assumed by the probe in the body and further based on an expected voltage value compared to the measured voltage measurement, selecting a shape based on the cost function, generating corrected coordinates of the points along the probe based on the shape and displaying a representation of the probe using the corrected coordinates.

BRIEF DESCRIPTION OF THE DRAWINGS

A more detailed understanding can be had from the following description, given by way of example in conjunction with the accompanying drawings wherein.

DETAILED DESCRIPTION

Implementations of the disclosed subject matter enable a medical professional to more accurately visualize a flexible probe (e.g., flexible magnetic loop sensor (FLS)) in a body of a subject by applying a model of the mechanical properties of the probe to apparent coordinates received from points on the probe. A processor first applies the model of known mechanical properties of the probe to the apparent coordinates, in order to compute a cost function with respect to shapes that can be assumed by the probe in the body. The processor then chooses a shape for the probe, responsively to the cost function, and then generates a set of corrected coordinates of the points along the length of the probe based on the shape. Using the corrected coordinates, a more accurate representation of the probe can be displayed.

Traditional magnetic based location detection systems utilize the sensors on a catheter (e.g., a mapping catheter) in combination with an algorithm to estimate the position and shape of the catheter, based on voltage measurements taken by the sensors. Such estimations are, for example, disclosed in U.S. Pat. No. 8,478,379 to Osadchy, which is incorporated herein by reference.

According to implementations of the disclosed subject matter, a catheter may include several flexible magnetic loop sensors (FLS). A FLS may sense the field of, for example, 9 transmitters that result in a total of 9 measurements taken at a single point (i.e., 9×1=9) per FLS sensor, while the FLS sensor is inside a patient's body. For example, for a catheter with 3 loops, it may be possible to place three FLS loops around the catheter by adding sensor wire to the three loops.

Figure 2A:
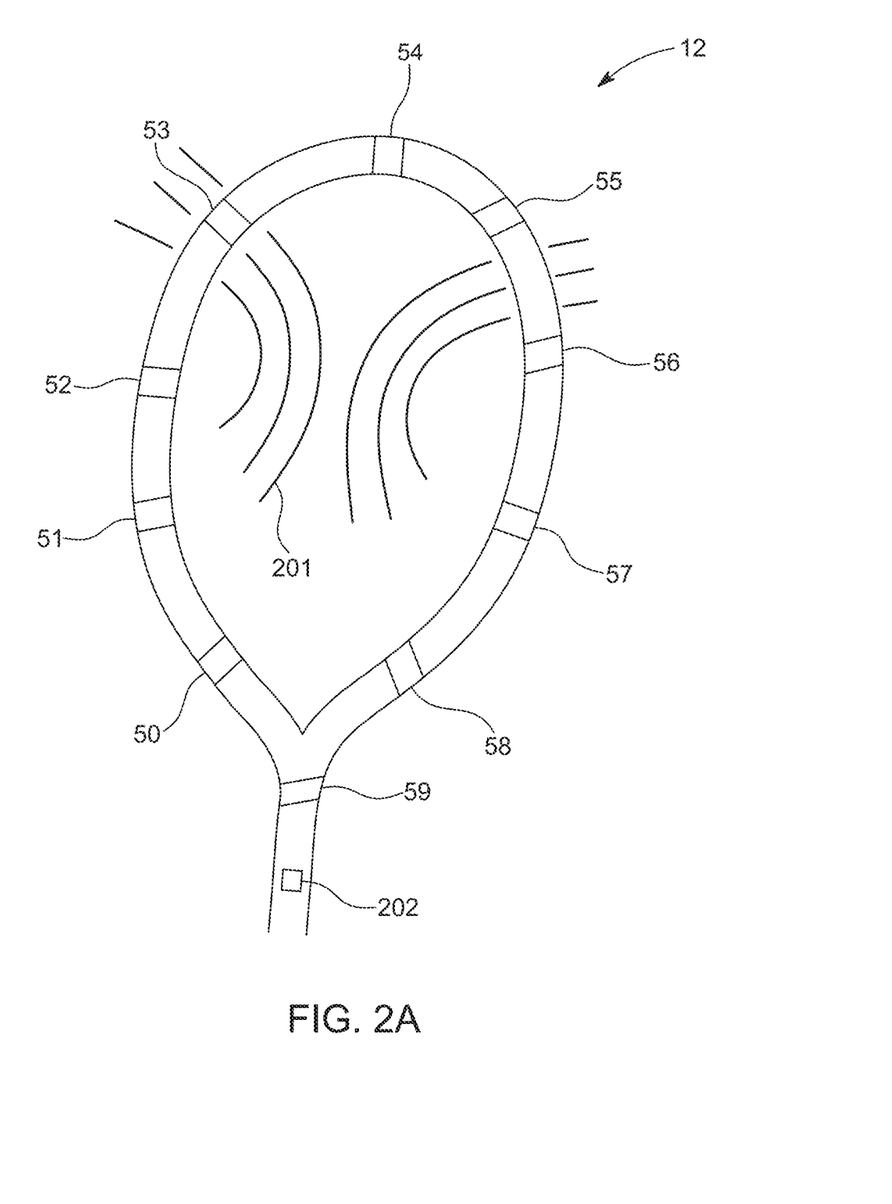
FIG. 2A is a schematic side view of an FLS probe deviating from its free shape, in accordance with implementations of the disclosed subject matter.

A catheter mechanics algorithm may define a catheter's parameters, such as an FLS loop catheter shown in FIG. 2A. The algorithm combines characteristics known in advance, such as the catheter's shape, its bendability and/or flexibility, the lengths of its various parts, and the like. The catheter's properties can be compared with actual measurements taken based on position and/or orientation of a sensor. Based on the catheter properties and the actual measurements, a cost function may be created, as further disclosed herein.

A first term (location errors) of the cost function may be the difference between the estimated positions and/or orientations of a sensor based on currently estimated shape of the catheter and the actual measurements from those sensors. This difference may be minimized to obtain a best match between the estimated position and the actual measurements for the positions. The catheter mechanics algorithm may be used to estimate the shape and position of the catheter in space, such that it defines where each sensor is located in space, based on the parameters of the catheter. The cost function is the error between the locations and the actual measurements of those locations. A best match of the shape to the actual measurements will minimize the cost function, such that the lowest cost function is obtained, with the lowest possible value.

A second term (mechanics or distortion) of the cost function includes the cost of distortion of the catheter. When the distortion is minimized, the resulting catheter will have a predetermined shape (e.g., it will be the loop of a FLS catheter). This second term that incorporates the distortion of a catheter may prevent the catheter mechanics algorithm from generating very distorted catheter shapes in order to match noisy or erroneous measurements from the sensors.

Inputs for the first term and the second term of the cost function include the position and orientation of a given sensors which are compared to known catheter parameters. According to implementations of the disclosed subject matter, an additional input to the catheter mechanics algorithm includes the voltage measurements of FLS loops embedded in the catheter. The voltage measurements may be sensed from a voltage contact that is part of or external to a FLS loop or other probe. Although the disclosure provided herein is directed to a single FLS loop for simplicity, it will be understood that the same disclosure can be applied to a catheter (e.g., catheter in FIG. 2C) with multiple FLS loops.

According to implementations of the disclosed subject matter, a catheter (e.g., FLS loop catheter) may be inserted into a patient's body (e.g., into a cardiac chamber). The magnetic field generated at a given location may be known based on any applicable technique such as via a location pad located below or near the patient's body, by body patches, calibration data, or the like or a combination thereof. Accordingly expected magnetic field received at the catheter (e.g., FLS loop catheter) may be known. The catheter mechanics algorithm may apply the expected magnetic field to calculate the expected voltage measurement from any FLS loop embedded in the catheter, based on the currently estimated catheter shape. To clarify, the known magnetic field generated at the location of the catheter (e.g., as determined by location pad calibration data) may be applied to the estimated shape of the catheter to determine the expected voltage from a FLS loop of a catheter. Further, the measured voltage at the FLS loop of the catheter may also be received based on a voltage reading of the FLS loop. The measured voltage may be measured from a voltage contact that is part of the FLS loop or external to the FLS loop.

The difference between the measured voltage (e.g., from a voltage contact) and expected voltages may be added to the first term and second term cost function such that the Cost (shape, position)=Location Errors+Mechanics (distortion)+ Magnetic Error (voltage difference). By minimizing the cost function, the catheter mechanics algorithm may determine the catheter position and shape that has the best match to the position sensors and FLS voltage measurements while considering mechanical properties of the catheter. Each FLS loop provides a plurality (e.g., 9) measurement which may be equivalent, in terms of degrees of freedom, to 3 Accurate Current Location (ACL) position sensors.

Figure 1:
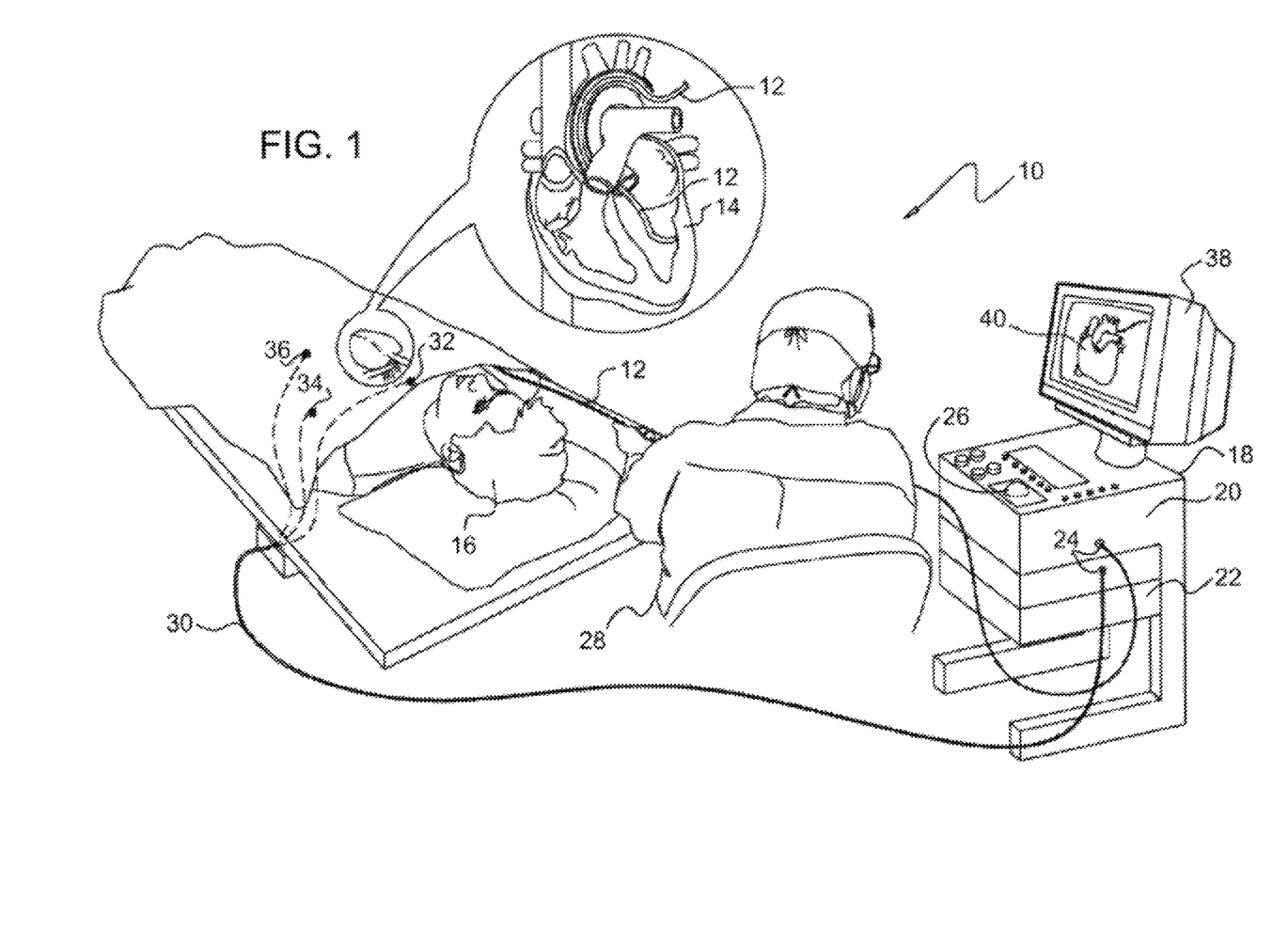
FIG. 1 is a schematic illustration of a position sensing system, in accordance with implementations of the disclosed subject matter.

FIG. 1 is an illustration of a position sensing system 10, which is constructed and operative in accordance with a disclosed subject matter. System 10 is used in determining the position of a flexible probe 12 such as an FLS catheter, which is inserted into an internal body cavity, such as a chamber of a heart 14 in a subject 16. Typically, probe 12 is used for diagnostic or therapeutic treatment, such as mapping electrical potentials in heart 14 or performing ablation of heart tissue. Probe 12 or other intrabody devices may alternatively be used for other purposes, by itself or in conjunction with other treatment devices. The distal tip of probe 12 comprises one or more electrodes (FIG. 2A). These electrodes are connected by wires (not shown) through the insertion tube of probe 12 to driver circuitry in a control unit 18, as described herein.

Control unit 18 is connected by wires through a cable 30 to body surface electrodes, which typically comprise adhesive skin patches 32, 34, 36. In alternative embodiments of the invention, the electrodes on the body surface may vary in number and may take other forms, such as subcutaneous probes or a handheld device operated by a medical professional 28. Patches 32, 34, 36 may be placed at any convenient locations on the body surface in the vicinity of probe 12. For example, for cardiac applications, patches 32, 34, 36 are typically placed around the chest of subject 16. There is no special requirement regarding the orientation of patches relative to each other or to the coordinates of the body, although greater accuracy may be achieved if the patches are spaced apart, rather than clustered in one location. There is no requirement that the placement of the patches be along fixed axes. Consequently, patch placement can be determined in order to interfere as little as possible with the medical procedure being performed.

Control unit 18 determines position coordinates of probe 12 inside heart 14 based on the impedance measured between probe 12 and patches 32, 34, 36. Additionally, the control unit 18 receives voltage values generated by the loop of a probe 12, based on a magnetic field at the location of the probe 12. Control unit 18 drives a display 38, which shows the position of probe 12 inside subject 16. Probe 12 may be used in generating a map 40 of the heart. The position of probe 12 may be superimposed on map 40 or on another image of the heart.

Control unit 18 is a computer system comprising a processor, such as a central processing unit (CPU) 20, which is programmed in software to carry out the functions that are described herein. Control unit 18 also includes a magnetic or semiconductor-based storage device 22 for storing application programs and data. A data I/O communications interface 24 enables control unit 18 to interact with probe 12 and patches 32, 34, 36. Medical professional 28 controls the operation of control unit 18 via a group of input devices 26.

It will be understood that although a single given component (e.g., control unit 18, storage device 22, etc.) are disclosed for simplicity, multiple such components may be used to implement the disclosed subject matter. For example, a first control unit 18 may determine position coordinates of probe 12 inside heart 12 and a second control unit 18 may receive the voltage values generated by the loop of a probe 12.

Although FIG. 1 shows a particular system configuration, other system configurations can also be employed to implement embodiments of the present invention and are thus considered to be within the spirit and scope of this invention. For example, the methods described herein may be applied in correcting position measurements made using position transducers of other types, such as magnetic or ultrasonic position sensors. The term "position transducer" as used herein refers to an element mounted on the probe which causes control unit 18 to receive signals indicative of the coordinates of the element. The position transducer may thus comprise a receiver on the probe, which generates a position signal to the control unit based on energy received by the transducer; or it may comprise a transmitter, emitting energy that is sensed by a receiver external to the probe. Furthermore, the methods described herein may similarly be applied in visualizing the locations not only of catheters, but also of probes of other types, both in the heart and in other body organs and regions.

The flowcharts and block diagrams in the figures illustrate the architecture, functionality, and operation of possible implementations of systems, methods and computer program products according to various embodiments of the present invention. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or by combinations of special purpose hardware and computer instructions.

Figure 2B:
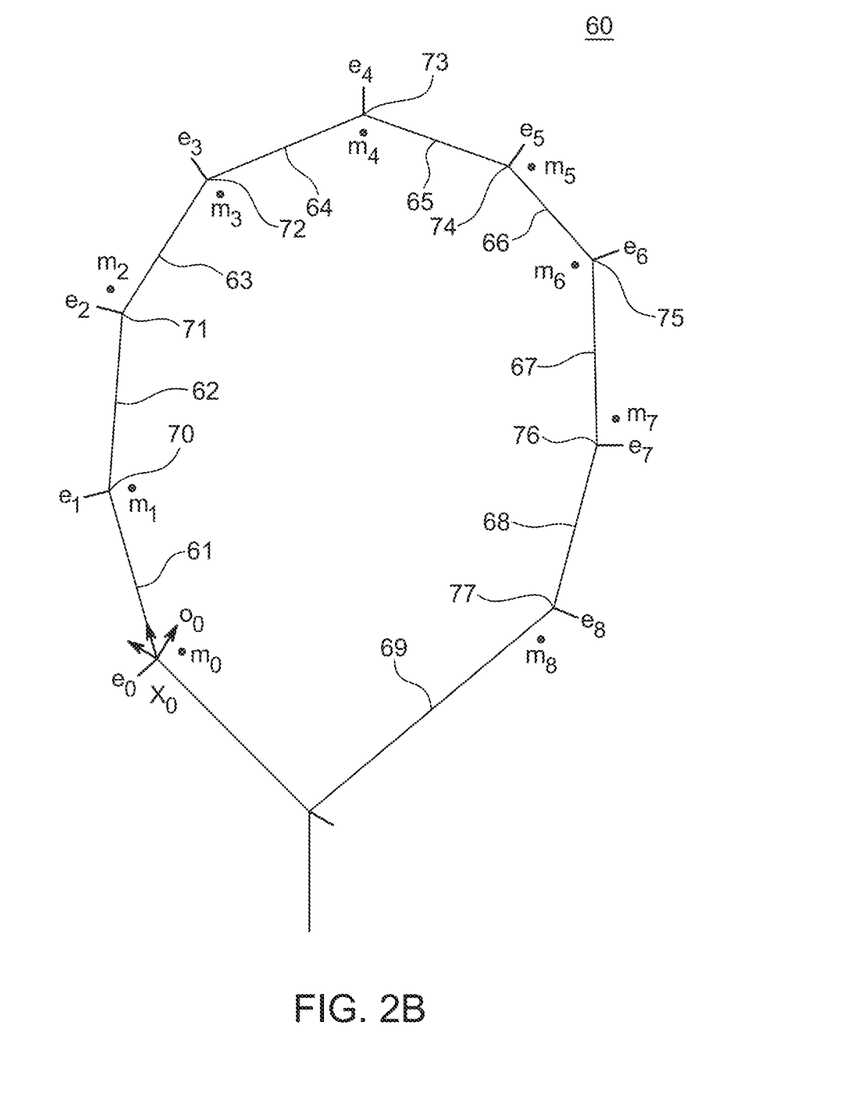
FIG. 2B is a diagram that schematically shows the model geometry of a probe deviating from its free shape, in accordance with implementations of the disclosed subject matter.

FIGS. 2A and 2B are diagrams that schematically show probe 12 deviating from its free shape, in accordance with an embodiment of the present invention. As shown in FIGS. 2A and 2B, the probe 12 is an FLS catheter comprising a FLS loop. FIG. 2A shows a representation of the actual curvature of probe 12 in heart 14, where probe 12 comprises electrodes 50, 51, 52, 53, 54, 55, 56, 57, and 58, which serve as position transducers in this implementation. The terms "electrodes" and "transducers" are used herein interchangeably for electrodes 50, 51, 52, 53, 54, 55, 56, 57, and 58 as they may also function as transducers. An additional electrode 59 may be provided that may provide position information about the base of the probe 12. As also shown in FIG. 2A, a voltage measurement area 202 may be provided and may indicate the voltage generated by the probe 12 based on a magnetic field 201 that is generated around the probe 12. The voltage measurement area 202 may be a voltage contact such as a conductive pad or a wired connection to, for example, control unit 18, such that the voltage generated by the probe is provided to analyze the cost function, as further disclosed herein.

FIG. 2B is a diagram of a calculated geometrical model 60 of probe 12. The measured locations of electrodes 50, 51, 52, 53, 54, 55, 56, 57, and 58, based on the signals received by control unit 18, are respectively represented by points $m_0$, $m_1$, $m_2$, $m_3$, $m_4$, $m_5$, $m_6$, $m_7$, and $m_8$. Alternatively, or additionally, in a magnetic position sensing system, the position transducers may comprise three-axis magnetic sensors (TAS), which provide position and a complete orientation matrix.

In model 60, points $e_0$, $e_1$, $e_2$, $e_3$, $e_4$, $e_5$, $e_6$, $e_7$, and $e_8$ represent calculated locations of electrodes 50, 51, 52, 53, 54, 55, 56, 57, and 58 based on the measured locations of points $m_0$, $m_1$, $m_2$, $m_3$, $m_4$, $m_5$, $m_6$, $m_7$, $m_8$, and $m_9$. A cost function in accordance with an embodiment of the present invention is used to find the best match between the point $e_j$ and $m_j$. Model 60 comprises straight rigid sections 61, 62, 63, 64, 65, 66, 67, 68, and 69, connected by joints 70, 71, 72, 73, 74, 75, 76, and 77 which allow rotation (bending and twisting).

The position of section 61 is described by position vector $x_0$, and the orientation of section 61 is given by a matrix $o_0$. Orientation matrix $o_0$ is a local reference frame of section 61 with its $\{\hat{x}\}$ and y axes being perpendicular to section 61, and the $\{\hat{z}\}$ axis pointing along section 61. Section 62 starts at the end of section 61 (i.e., via connecting joint 70), and its orientation is given by matrix $o_1$. Section 63 starts at the end of section 62 (i.e., via connecting joint 71), and its orientation is given by matrix $o_2$. This arrangement continues through until each of the sections 61 through 69 starts at the end of the respective previous section and has respective connecting joints 70-78. Matrices $o_0$ through $o_8$ describe the actual state (i.e., shape) of the probe, such that external forces cause the probe to deviate from its free state in which no external forces are applied to the probe. Although model geometry 60 comprises three sections, alternative model geometries may comprise either fewer than eight or more than eight sections.

According to implementations of the disclosed subject matter, the best match between the points $e_j$ and the measurements $m_j$ is determined within the constraints of a probe model. Note that the calculated locations of points $e_0$ through $e_8$ are constrained by the model to be on the sections 61 through 69, but the actual position transducers (i.e., electrodes 50 through 58) may not be precisely at these points. The physical properties of probe 12 in its free state are defined by the parameters $\{N, L_k, G_k(d), P_k\}$ where:

N—Number of sections.

$L_k$—Section lengths (need not be equal), $0 \leq k < N$.

$G_k(d)$—Rotation matrix as a function of the deflection parameters d for deflectable probes (or a constant matrix for pre-shaped probes), $1 \leq k < N$. This matrix represents the relative rotation between section k and section (k−1) when no external forces are applied (i.e., a probe's free shape).

$P_k$—List of position transducers on section k, where $0 \leq k < N$. Each position transducer is represented by its distance from the section start, its type (for example, FLS or TAS magnetic sensor), and its relative importance (its weight in calculating a cost function, denoted by $w_j^{model}$, discussed herein). The list for each section can contain any number of position transducers, including zero.

The physical properties of probe 12 are described by the parameters $\{A_k, B_k\}$ which represent the resistance of a joint between section k and section (k−1) against bending and twisting, respectively.

Frequently, as shown in FIG. 2B, the actual position of probe 12 (as defined by the locations of electrodes 50 through 58) differs from points $m_0$ through $m_8$. According to implementations of the disclosed subject matter, a probe model is defined, describing the physical characteristics of probe 12, and CPU 20 applies a probe mechanics algorithm to achieve the best match between the probe model and the measurements. The result is a minimal cost state for probe 12, which describes the location and shape (i.e., an actual shape different from the free shape) of probe 12 and its deflection values (for a deflectable probe). A deflection value is a model parameter that describes a family of probe free shapes for a deflectable probe. Typically, a single deflection parameter affects several joints. Any joint rotation that differs from the rotation defined by the deflection parameter increases the cost function.

The probe mechanics algorithm uses a cost function, which is a weighted combination of intrinsic energy, position error and orientation error. Intrinsic energy represents the deviation of probe 12 from its free shape. Position error represents the error in position coordinates between the position transducer locations, given by the probe model and state, and the actual position measurements. Finally, orientation error represents the error in angular orientation coordinates between the position transducer orientations, given by the probe model and state, and the actual orientation measurements.

Figure 2C:
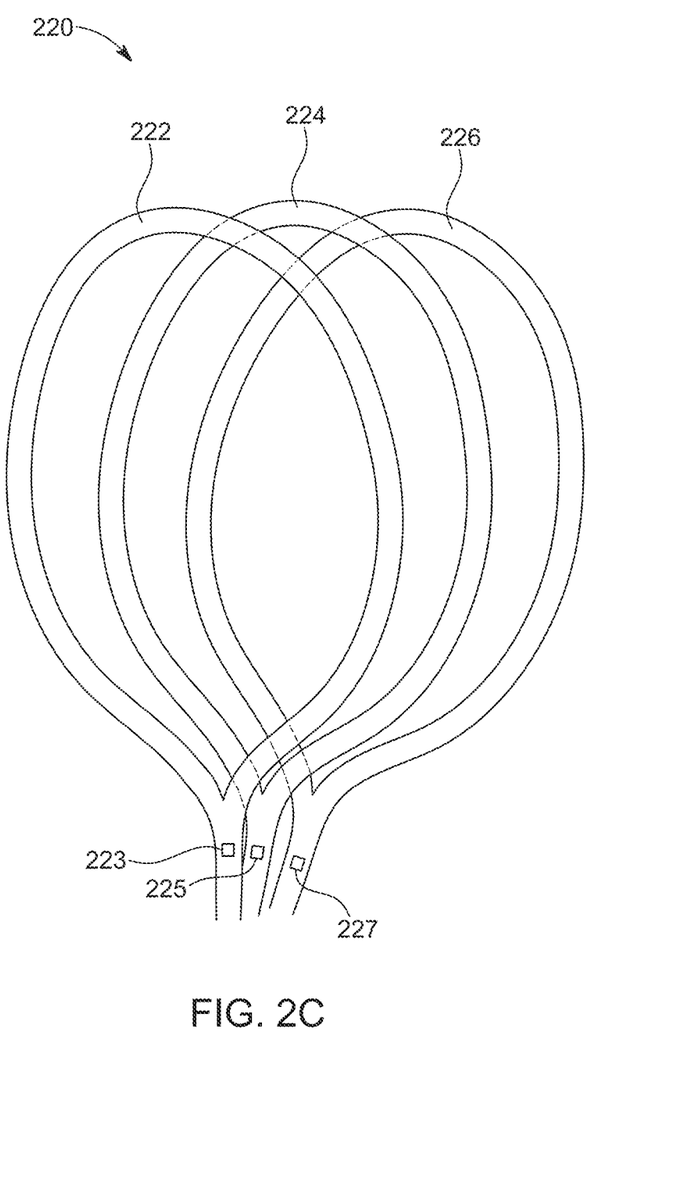
FIG. 2C is a diagram that shows multiple FLS probes as part of a catheter, in accordance with implementations of the disclosed subject matter.

FIG. 2C shows an implementation of the disclosed subject matter that includes a probe 220 that has multiple FLS loops 222, 224, 226. Each of the FLS loops may generate a voltage amount based on a magnetic field at the location of the respective FLS loop. The voltage reading for each of the FLS loops 222, 224, and 226 may be provided at connection point 223, 225, and 227 respectively. As further disclosed herein, the expected voltage may be compared to the measured voltage for each FLS loop and may be a factor in the cost function.

Figure 3:
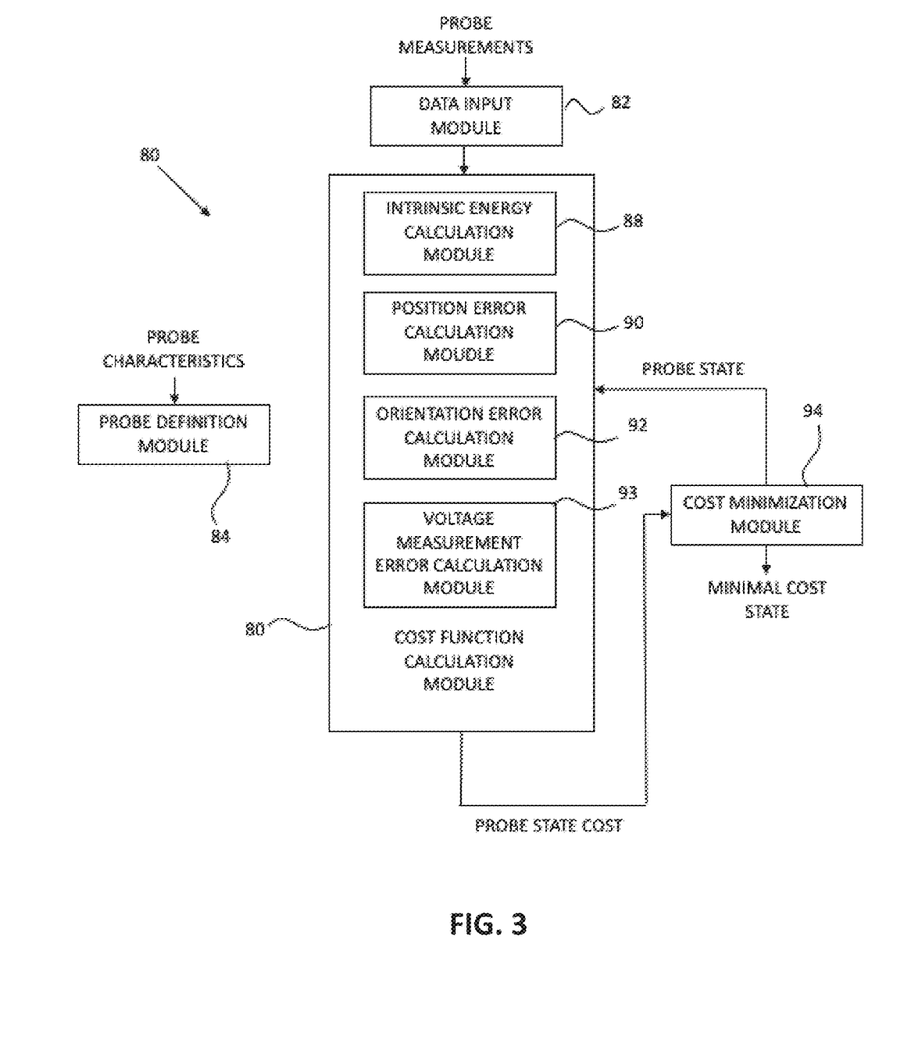
FIG. 3 is a diagram that schematically shows details of a probe visualization system, in accordance with implementations of the disclosed subject matter.

FIG. 3 is a block diagram 80 that schematically illustrates functional components of system 10 that are used in detection and compensation for artifacts experienced during position sensing of a probe, in accordance with an implementation of the disclosed subject matter. Specifically, this figure shows functional elements of software and/or firmware that runs on CPU 20 or a different component with a processor, to determine the position of probe 12 based on measured verses expected values as well as a cost function. These functional elements are described in greater detail with referenced to the figures below.

Figure 4:
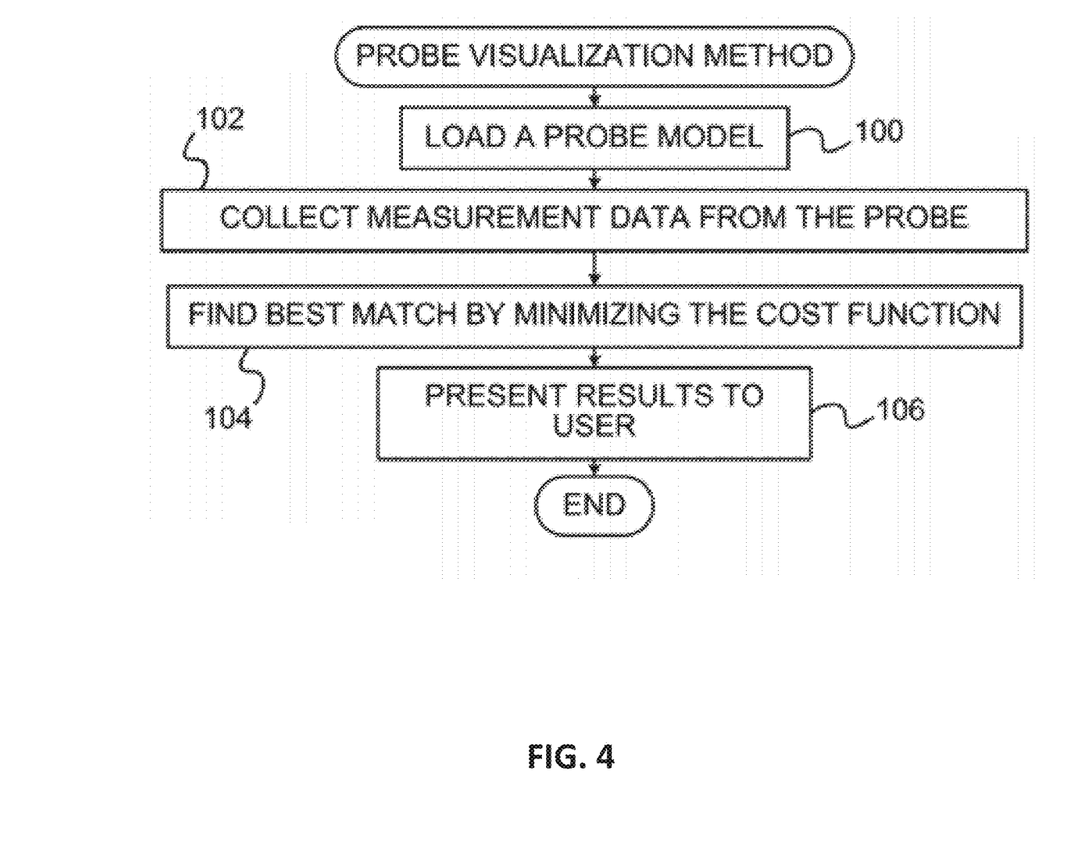
FIG. 4 is a flow diagram illustrating a probe visualization method, in accordance with implementations of the disclosed subject matter.

FIG. 4 is a flow chart that schematically illustrates a method for visualizing probe 12 placed within subject 16, in accordance with an implementation of the disclosed subject matter. First, a probe model is pre-loaded into a probe definition module 84 at step 100. As discussed herein, the probe model describes the structure and the physical properties of probe 12 and is typically defined specifically for the type of catheter or another probe that is to be used. The probe model may include the structure and physical properties of a multiple FLS loop probe. According to an implementation, a medical professional 28 may select the model, for example, from a predefined list of options.

As the probe 12 moves within subject 16, at step 102, a data input module 82 collects output position signals from electrodes 50-58 at regular intervals. For each position transducer 50-58 defined in the probe model, data input module 82 receives a corresponding position measurement. The measurement can include a position vector (all types of transducers), direction (FLS) and/or full orientation (TAS). In addition, a measurement weight is associated with each measurement, depending on the confidence level of the measurement. The weight has a high value for precise measurements, and a low value for measurements with large expected error. Missing measurements will have weight of zero. The measurement parameters include:

$m_j$—Position measurement $m_j^{or}$—Orientation measurement (may include the full orientation or only direction)

$w_j^{msr}$—Weight of the measurement

After data input module 82 receives the inputs, at step 104 a cost function calculation module 86 defines a probe state cost by applying a cost function to calculate the quality of the match between the probe model defined in probe definition module 84 and position data received from data input module 82. This match defines the shape of the probe with the lowest cost according to the model, which in turn gives corrected coordinates of the points along the length/boundary of the probe that correspond to the locations of the position transducers. The probe state describes the location and shape of probe 12 and its deflection values (for a deflectable probe). CPU 20 or other applicable component that includes a processor determines the probe state at step 104. The state is given by the variables $\{x_0, r_k, d\}$:

$x_0$—The position of the first section starting point (e.g., in FIG. 2B).

$r_k$—The orientation of section k relative to section k−1 for $0<k<N$ and the global orientation of the first section for k=0:

$$r_k = \begin{cases} O_{k-1}^T \cdot O_k & 0 < k < K \\ O_0 & k = 0 \end{cases} \quad (1)$$

d—The values of the deflection parameters (for deflectable probes). These values do not affect the position and shape of probe 12, but they do affect the calculation of the cost function and thus affect the outcome of the probe mechanics algorithm. As part of step 104, cost function calculation module 86 feeds the probe state cost to a cost minimization module 94, which applies a minimization algorithm to the cost function in order to find a minimal cost probe state that achieves a minimum value of the cost function (i.e., a best match). Finally, after determining the minimal cost probe state, display 38 presents map 40, showing the position of probe 12 in subject 16, at step 106. For example, the probe position may be shown in the form of an icon on the display, having a location, orientation and shape corresponding to model 60.

Figure 5:
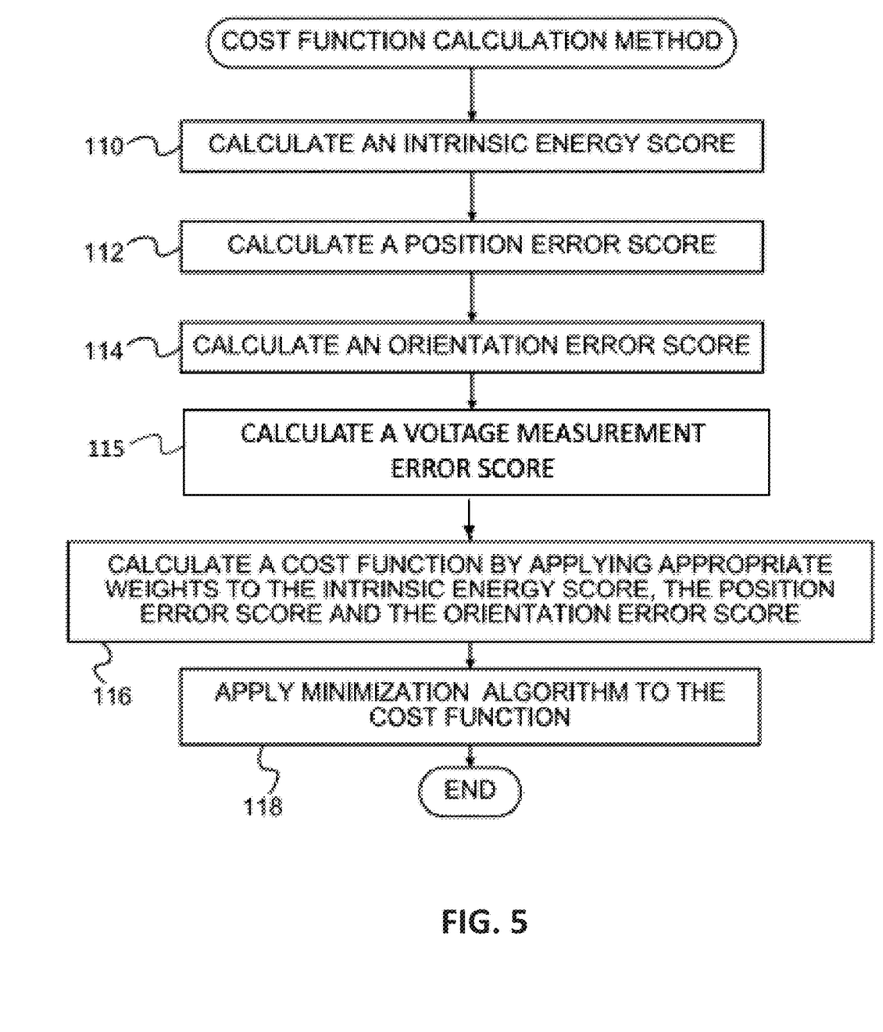
FIG. 5 is a flow diagram illustrating a cost function calculation method, in accordance with implementations of the disclosed subject matter.

FIG. 5 is a flow chart that schematically illustrates a method by which cost function calculation module 86 applies a cost function to probe measurements received by data input module 82, in accordance with an embodiment of the present invention. The cost function depends on the probe model, the position measurements, the probe state, and the voltage output from the probe. Minimizing the cost function with respect to the probe state $\{x_0, r_k, d\}$ and the voltage output achieves the best match between the probe model and the measurements. The calculation of the cost function also depends on a set of adaptive weights that are assigned to the measurements. The adaptive weights may dynamically change during the course of the cost function minimization and allow the algorithm to ignore measurements that totally disagree with the probe model (described hereinbelow). The adaptive weights are denoted by $w_j^{adaptive}$.

The cost function has four parts: intrinsic energy, position error, orientation error, voltage measurement error. First, an intrinsic energy calculation module 88 calculates an intrinsic energy score at step 110, which represents the deviation of probe 12 from its free shape (or a family of free shapes parameterized by deflection variables—for deflectable probes). For joints 70 through 77, the orientation difference between the actual relative orientation and the current deflection is calculated as:

$$dr_k = r_k \cdot G_k(d) \quad (2)$$

Intrinsic energy calculation module 88 converts this orientation difference to the bend and twist angles:

$$\{\alpha_k \beta_k\} = \text{Angles}(dr_k) \quad (2)$$

The following is a definition of the function Angeles (r) where r is a unitary 3×3 matrix that represents rotation:

$$\{\alpha_k, \beta_k\} = \text{Angles} \begin{pmatrix} r_{11} & r_{12} & r_{13} \\ r_{21} & r_{22} & r_{23} \\ r_{31} & r_{32} & r_{33} \end{pmatrix} \quad (3)$$

-continued $$\alpha = arcos(r_{33}) \quad (4)$$

$$\beta = \arctan(r_{11}(1+r_{33}) - r_{31}r_{13}, r_{12}(1+r_{33}) - r_{32}r_{13}) \quad (5)$$

Where:

arctan(x,y) is the angle between the vector (x,y) and the x axis (6)

Returning to the cost function, intrinsic energy calculation module 88 calculates the intrinsic energy score using the probe model parameters $\{A_k, B_k\}$:

$$E^{ira} = \Sigma_{k=1}^{N-1} A_k \alpha_k^2 + B_k \beta_k^2 \quad (7)$$

A position error calculation module 90 then calculates a position error score at step 112, which represents the position error between the locations of the position transducers given by the probe model and state, and the actual measurements. Position error calculation module 90 denotes the position of electrodes 50 through 58 according to the probe model and state as $e_j$ and the corresponding measurements as $m_j$. Position error calculation module 90 calculates the weighted position error as follows:

$$E^{pos} = \Sigma_{j=0}^{M-1} w_j^{model} w_j^{msr} w_j^{adaptive} (e_j - m_j)^2 \quad (8)$$

where M is the number of position transducers.

An orientation error calculation module 92 then calculates an orientation error score at step 114, which represents the orientation error between the position of electrodes 50-58, given by the probe model and state, and the actual measurements m received by data input module 82. The orientation of the various points along probe 12, represented by the probe model, is a discontinuous function, which has abrupt changes at model joints (unlike the position). After calculating the orientations of all the relevant position transducers $e_j^{or}$ according to the model, orientation error calculation module 92 calculates the angular difference with respect to the measured orientation $m_j^{or}$:

$$\{a_j, b_j\} = \text{Angles} ((e_j^{or})^T \cdot m_j^{or}) \quad (9)$$

and the total orientation error:

$$E^{or} = \Sigma_{j=0}^{M-1} w_j^{model} w_j^{msr} w_j^{adaptive} (a_j^2 + b_j^2) \quad (10)$$

A voltage measurement error calculation module 93 then calculates a voltage measurement error score at step 115, which represents the voltage measurement error between expected voltage measurement expected at from the probe 12 based on a known magnetic field at the location of the probe 12, and the actual voltage measurements received by data input module 82. The magnetic field generated at a given location may be known based on any applicable technique such as via a location pad located below or near the subject's body, by body patched, calibration data, or the like or a combination thereof. Accordingly expected magnetic field received at the probe 12 may be known. To clarify, the known magnetic field generated at the location of the catheter (e.g., as determined by location pad calibration data) may be applied to the measured shape of the probe 12 to determine the expected voltage from a FLS loop of a catheter. Further, the measured voltage at the FLS loop of the catheter may be received based on a voltage reading at a portion (e.g., base) of the FLS loop.

A voltage measurement error calculation module 93 then calculates a voltage measurement error score at step 115, which represents the voltage measurement error between an expected voltage measurement expected from the probe 12 based on a known magnetic field at the location of the probe 12, and the actual voltage measurements received by data input module 82. The magnetic field generated at a given location may be known based on any applicable technique such as via a location pad located below or near the subject's body, by body patched, calibration data, or the like or a combination thereof. Accordingly expected magnetic field received at the probe 12 may be known. To clarify, the known magnetic field generated at the location of the catheter (e.g., as determined by location pad calibration data) may be applied to the measured shape of the probe 12 to determine the expected voltage from a FLS loop of a catheter. Further, the measured voltage at the FLS loop of the catheter may be received based on a voltage reading at a portion (e.g., base) of the FLS loop.

Induced voltage calculations may be based on the generated magnetic field represented by the magnetic vector potential $\vec{A}(\vec{r})$ where $\vec{r}$ is the space coordinate. This representation, for example, may take a form of multipole expansion in terms of vector spherical harmonics:

$$\vec{A}(\vec{r}) = \frac{\mu_0}{4\pi} \sum_{l,m} \frac{1}{r^{l+1}} \Phi_{l,m}(\vec{r} - \vec{r}_0) c_{l,m} \quad (11)$$

Where $\mu_0$ and $\pi$ are known constants, $\Phi_{l,m}$ are the vector spherical harmonics functions (derived from the scalar spherical harmonics by $\Phi_{l,m} = \vec{r} \times \nabla' Y_{l,m}$), $\vec{r}_0$ is the expansion center and $c_{l,m}$ are the expansion coefficients.

Thus, in order to calculate the magnetic vector potential, and the magnetic field, of a generating element at any point, the expansion center $\vec{r}_0$ and the expansion coefficients $c_{l,m}$ of the field generator may be provided, for example, from a file or in a persistent memory. According to the example disclosed herein, 9 field generating elements may be provided, and the magnetic fields may be completely described by the expansion centers $\vec{r}_0^k$ and expansion coefficients $c_{l,m}^k$, where k is the index of the magnetic field generating element. The vector potentials of the field generators are calculated as:

$$\vec{A}^k(\vec{r}) = \frac{\mu_0}{4\pi} \sum_{l,m} \frac{1}{r^{l+1}} \Phi_{l,m}(\vec{r} - \vec{r}_0^k) c_{l,m}^k \quad (12)$$

The voltage that is induced in a wire loop due to magnetic field can be calculated by line integration of the magnetic vector potential over the loop: $V^k = \Phi \vec{A}^k(\vec{r}) \cdot d\hat{l}$, where the loop geometry is given by the current state of the catheter mechanics algorithm. The line integral can be evaluated by any known numerical methods, for example it can be approximated as a sum $$V^k = \sum_{i=1}^{n-1} \vec{A}^k \left( \frac{\vec{r}_i + \vec{r}_{i+1}}{2} \right) \cdot (\vec{r}_{i+1} - \vec{r}_i),$$

where $\vec{r}_i$ are points along the currently estimated shape of the loop.

The voltage error part of the cost function is calculated as sum of squared differences between expected and measured voltages:

$$E^{vm}=\Sigma_k(V^k-M^k)^2 \quad (13)$$

where $V^k$ is the expected voltage on the FLS (calculated as described above) and $M^k$ is the measured voltage and k is the index of the field generator.

Cost function calculation module 86 then calculates a cost function as a weighted combination of the four parts (i.e., intrinsic energy, position error, orientation error, voltage measurement) (i.e., step 116):

$$\text{Cost}(x_0,r_k,d)=\lambda^{int}E^{int}+\lambda^{pos}E^{pos}+\lambda^{or}E^{or}+\lambda^{vm}E^{vm} \quad (14)$$

The values $\{\lambda^{int}, \lambda^{pos}, \lambda^{or}, \lambda^{vm}\}$ describe the relative importance of deviation of probe 12 from its free shape vs. the position and orientation errors.

As discussed herein, cost function calculation module 86 feeds the calculated cost function (i.e., the probe state cost) to minimization module 94, which minimizes the function Cost ($x_0$, $r_k$, d) with respect to the probe state variables in order to achieve the best match between the probe model and the actual measurements received by data input module 82, at step 118. The minimization can be done by any suitable numerical method. According to an implementation, for example, cost function calculation module 86 uses the Broyden-Fletcher-Goldfarb-Shanno (BFGS) minimization algorithm.

Since minimizing the cost function in step 118 employs an iterative algorithm (i.e., each iteration of the algorithm improves the estimate of the solution), and the position and shape of probe 12 change slowly between measurements, it may be sufficient to apply only one iteration of the cost function minimization algorithm for each successive measurement. After each minimization iteration, cost minimization module 94 feeds a probe state to cost function calculation module 86, which may change the adaptive weights of the measurements according to the individual transducer position errors. Typically, the weights corresponding to impedance-sensing electrodes are adapted, while more accurate sensors, such as magnetic position sensors, retain a weight of 1.

Cost function calculation module 86 performs the weight adaptation procedure as follows:

1. Compute Initial New Weights $$w_j^{new} = \max\left(\exp\left(\frac{(e_j-m_j)^2}{2\sigma_j^2}\right)\cdot 0.0001\right) \quad (15)$$

where the value σ is larger for sensors with a large expected error, thereby allowing a greater error prior to a decrease in a corresponding adaptive weight.

2. Normalize the Initial Weights $$w_j^{new} \leftarrow \frac{w_j^{new}}{\text{mean}(w_j^{new})} \quad (16)$$

3. Limit each Weight from above by 1

$$w_j^{new} \leftarrow \min(w_j^{new},1) \quad (17)$$

4. Update the Adaptive Weights $$w_j^{adaptive} \leftarrow 0.9 w_j^{adaptive}+0.1 w_j^{new} \quad (18)$$

This adaptation procedure allows the minimization process to ignore position transducers that consistently give large errors yet does not allow it to ignore too many position transducers.

According to an embodiment, the cost function may be computed based on the intrinsic energy and the voltage measurement such that the position error and orientation error need not be required to obtain an optimal cost function. The intrinsic energy and the voltage measurement may be calculated in accordance with the techniques disclosed herein.

According to this embodiment an intrinsic energy representation a deviation of the probe from a free shape of the probe may be calculated as disclosed herein. Additionally, a voltage measurement error between the expected voltage value based on a known magnetic field at a probe location and the measured voltage may be calculated, as disclosed herein. Accordingly, a cost function may be calculated as a weighted sum of the intrinsic energy and voltage measurement error. The equation for this embodiment can be represented by:

$$\text{Cost}(x_0,r_k,d)=\lambda^{int}E^{int}+\lambda^{vm}E^{vm} \quad (19)$$

Any of the functions and methods described herein can be implemented in a general-purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer-readable media). The results of such processing can be maskworks that are then used in a semiconductor manufacturing process to manufacture a processor which implements features of the disclosure.

Any of the functions and methods described herein can be implemented in a computer program, software, or firmware incorporated in a non-transitory computer-readable storage medium for execution by a general-purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

The invention claimed is:

1. A method for visualization of a probe having a plurality of position transducers inside a body of a subject, comprising:
generating a magnetic field;
receiving a plurality of measured coordinates from the plurality of position transducers;

generating, by the probe, a voltage measurement based on the magnetic field detected around the probe;
calculating magnetic vector potentials of the magnetic field;
determining a cost function based on a model of known mechanical properties of the probe compared to the measured coordinates with respect to shapes that can be assumed by the probe in the body and on an expected voltage value compared to the voltage measurement;
selecting a shape based on the cost function;
calculating a voltage measurement error between the expected voltage value and the voltage measurement;
generating corrected coordinates of the plurality of position transducers of the probe based on the shape and the voltage measurement error between the expected voltage value and the voltage measurement; and
displaying a representation shape of the probe using the corrected coordinates, and wherein the expected voltage value is determined using the magnetic vector potentials at the plurality of measured coordinates and points along an estimated shape of the probe.

2. The method of claim 1, wherein the cost function is computed based on:
calculating an intrinsic energy representing a deviation of the probe from a free shape of the probe;
and calculating the cost function as a weighted sum of the intrinsic energy and the voltage measurement error.

3. The method of claim 2, wherein the cost function is further computed based on:
calculating a position error between the model of known mechanical properties of the probe and the input;
calculating an orientation error between the model of known mechanical properties of the probe and the input; and
further calculating the cost function as a weighted sum of the position error and the orientation error.

4. The method of claim 1, wherein the probe comprises at least one flexible loop sensor.

5. The method of claim 1, wherein the probe comprises a catheter, and wherein receiving the input comprises receiving a measurement of apparent coordinates of the catheter within a heart of the subject.

6. The method of claim 1, wherein the input is selected from at least one of a position vector, a direction measurement, or a full orientation measurement.

7. The method of claim 2, wherein the voltage measurement is generated by a voltage contact on the probe based on the magnetic vector potentials of the generated magnetic field at the plurality of measured coordinates using a known magnetic field passing through a loop of the probe and points along an estimated shape of the probe.

8. The method of claim 1, wherein the probe comprises at least one of a single-axis magnetic sensor and a three-axis magnetic sensor.

9. The method of claim 1, wherein the model of known mechanical properties of the probe comprises:
multiple sections of the probe;
a length of each of the sections;
a rotation matrix defining relative rotation of each of the sections with regard to a preceding section; and
a location on the probe of each of the plurality of position transducers.

10. The method of claim 9, wherein the rotation matrix comprises a function of one or more deflection parameters of the probe.

11. A system for visualization of a probe inside a body of a subject, the system comprising:
the probe comprising a plurality of position transducers and a voltage contact;
a processor, the processor configured to:
receive a plurality of measured coordinates from the plurality of position transducers;
generate a voltage measurement generated and output by the probe based on a generated magnetic field detected around the probe;
calculate magnetic vector potentials of the generated magnetic field;
determine a cost function based on a model of known mechanical properties of the probe compared to the measured coordinates with respect to shapes that can be assumed by the probe in the body and on an expected voltage value compared to the voltage measurement;
select a shape based on the cost function;
calculating a voltage measurement error between the expected voltage value and the voltage measurement;
and generate corrected coordinates of the plurality of position transducers of the probe based on the shape and the voltage measurement error between the expected voltage value and the voltage measurement,
wherein the expected voltage value is determined using the magnetic vector potentials at the plurality of measured coordinates and points along an estimated shape of the probe.

12. The system of claim 11, further configured to provide, for display, a representation shape of the probe using the corrected coordinates, wherein the cost function is computed based on: calculating an intrinsic energy representing a deviation of the probe from a free shape of the probe; and calculating the cost function as a weighted sum of the intrinsic energy and the voltage measurement error.

13. The system of claim 12, wherein the cost function is further computed based on:
calculating a position error between the model of known mechanical properties of the probe and the input;
calculating an orientation error between the model of known mechanical properties of the probe and the input; and
further calculating the cost function as a weighted sum of the position error and the orientation error.

14. The system of claim 11, wherein the probe comprises a catheter, and wherein receiving the input comprises receiving a measurement of apparent coordinates of the catheter within a heart of the subject.

15. The system of claim 11, wherein the input is selected from at least one of a position vector, a direction measurement and a full orientation measurement.

16. The system of claim 12, wherein the voltage measurement is generated by the voltage contact based on the magnetic vector potentials of the generated magnetic field at the plurality of measured coordinates using a known magnetic field passing through a loop of the probe and points along an estimated shape of the probe.

17. A probe visualization apparatus, comprising:
a data I/O communications interface configured to receive an input of a plurality of measured coordinates of a respective plurality of position transducers of a probe, inside a body of a subject and further configured to receive a voltage measurement generated by and output by the probe, based on a generated magnetic field detected around the probe; and
a processor configured to:

receive the input from the data I/O communications interface;
calculate magnetic vector potentials of the generated magnetic field;
determine a cost function based on a model of known mechanical properties of the probe compared to the measured coordinates with respect to shapes that can be assumed by the probe in the body and further based on an expected voltage value compared to the voltage measurement;
select a shape based on the cost function;
calculating a voltage measurement error between the expected voltage value and the voltage measurement;
and generate corrected coordinates of the plurality of position transducers of the probe based on the shape and the voltage measurement error between the expected voltage value and the voltage measurement,
wherein the expected voltage value is determined using the magnetic vector potentials at the plurality of measured coordinates and points along an estimated shape of the probe.

18. The apparatus of claim 17, further configured to provide, for display, a representation shape of the probe using the corrected coordinates, wherein the cost function is computed based on: calculating an intrinsic energy representing a deviation of the probe from a free shape of the probe; and calculating the cost function as a weighted sum of the intrinsic energy and the voltage measurement error.

19. The apparatus of claim 18, wherein the cost function is further computed based on:
calculating a position error between the model of known mechanical properties of the probe and the input;
calculating an orientation error between the model of known mechanical properties of the probe and the input; and
further calculating the cost function as a weighted sum of the position error and the orientation error.

20. The apparatus of claim 18, wherein the voltage measurement is generated by a voltage contact on the probe based on the magnetic vector potentials of the generated magnetic field at the plurality of measured coordinates using a known magnetic field passing through a loop of the probe and points along an estimated shape of the probe.

* * * * *

UNITED STATES PATENT AND TRADEMARK OFFICE
CERTIFICATE OF CORRECTION

PATENT NO. : 12,076,131 B2
APPLICATION NO. : 16/866883
DATED : September 3, 2024
INVENTOR(S) : Daniel Osadchy et al.

It is certified that error appears in the above-identified patent and that said Letters Patent is hereby corrected as shown below:

In the Specification

1. In Column 5, Line 50, delete "m5." and insert -- m8. --, therefor.
2. In Column 6, Line 1, delete "y" and insert -- ŷ --, therefor.
3. In Column 7, Line 24, delete "verses" and insert -- versus --, therefor.
4. In Column 7, Line 26, delete "referenced" and insert -- reference --, therefor.
5. In Column 8, Lines 9-11, delete " $r_k = \begin{cases} O_{k-1}^T \cdot O_k & 0 < k < K \\ O_0 & k = 0 \end{cases}$ " and insert -- $r_k = \begin{cases} O_{k-1}^T \cdot O_k & 0 < k < N \\ O_0 & k = 0 \end{cases}$ --, therefor.
6. In Column 8, Line 55, delete "$dr_k = r_k\tau \cdot G_k(d)$" and insert -- $dr_k = r_k\tau \cdot G_k(d)$ --, therefor.
7. In Column 8, Line 58, delete "{αkβk}=Angles (drk)" and insert -- {αk,βk}=Angles (drk) --, therefor.
8. In Column 8, Line 59, delete "Angeles" and insert -- Angles --, therefor.
9. In Column 10, Line 30, delete "$\Phi_{l,m} \vec{r} \times \nabla Y_{l,m})$," and insert -- $\Phi_{l,m} = \vec{r} \times \nabla Y_{l,m}$ ), --, therefor.
10. In Column 10, Line 54, delete "$V^k = \Phi \vec{A}^k(\vec{r}) \cdot d\hat{l}$," and insert -- $V^k = \oint \vec{A}^k(\vec{r}) \cdot d\vec{l}$ , --, therefor.
11. In Column 12, Line 13, delete "a" and insert -- of a --, therefor.

Signed and Sealed this
Fifth Day of November, 2024

Katherine Kelly Vidal
*Director of the United States Patent and Trademark Office*